United States Patent [19]

Hotta et al.

[11] Patent Number: 4,837,010

[45] Date of Patent: Jun. 6, 1989

[54] LONG WAVE UV RAY ABSORBER

[75] Inventors: Hajime Hotta, Yatabe; Michiyo Akasaka, Matsudo, both of Japan

[73] Assignee: Kao Corporation, Tokyo, Japan

[21] Appl. No.: 32,577

[22] Filed: Apr. 1, 1987

[30] Foreign Application Priority Data

Apr. 2, 1986 [JP] Japan .................................. 61-75923

[51] Int. Cl.$^4$ .......................... A61K 7/02; A61K 7/40; A61K 7/42; A61K 7/44

[52] U.S. Cl. ................................ 424/59; 424/DIG. 5; 424/60; 424/63; 424/64; 424/69; 514/844; 514/845; 514/937

[58] Field of Search ..................................... 424/59, 63

[56] References Cited

U.S. PATENT DOCUMENTS 4,710,373 12/1987 Nakamura et al. .................... 424/59

OTHER PUBLICATIONS

Derwent Abstract of Japanese Pat. No. 60094949, 10/1983, Tsudone et al.

Derwent Abstract of Japanese Pat. No. 60094936, Tsudone et al., (I).

Primary Examiner—Dale R. Ore
Attorney, Agent, or Firm—Oblon, Spivak, McClelland, Maier & Neustadt

[57] ABSTRACT

A novel long wave UV ray absorber comprising a dibenzoylmethane derivative effectively shuts out UV-A which causes a harmful action on skin.

The absorber is insoluble in water, organic solvents, oily substances, sebum and the like, so that percutaneous absorption does hardly take place and the absorber is scarcely removed by water or sweat, thus keeping a high efficacy.

4 Claims, No Drawings

LONG WAVE UV RAY ABSORBER

BACKGROUND OF THE INVENTION (1) Field of the Invention

This invention relates to a long wave UV ray absorber and more particularly to a long wave UV ray absorber containing a dibenzoylmethane derivative and also to a cosmetic composition comprising such absorber.

(2) Description of the Prior Art

It is known that UV ray brings about a variety of changes to the skin. Dermatologically, the UV ray is classified into a long wave UV ray of 400 to 320 nm, an intermediate wave UV ray of 320 to 290 nm and a short wave UV ray of below 290 nm, which are, respectively, called UV-A, UV-B and UV-C.

The most common UV ray source to which one is exposed is usually the sunlight. UV rays which reach the ground are UV-A and UV-B, and UV-C does rarely reach the ground because it is absorbed in the ozone layer. Among the UV rays which can reach the ground, the UV-B, if irradiated on the skin in an amount more than a certain level, red spots or blisters are formed. In addition, melanosis is promoted and the skin undergoes changes such as pigmentation. In contrast, UV-A has been considered not to cause a substantial change in the skin. However, it has been recently revealed by electron microscopic and histochemical techniques that the skin suffers changes by UV-A irradiation. Especially, unlike UV-B, UV-A allows its energy to reach the true skin and brings about slightly chronic changes in the blood walls and the elastic fibers of connective-tissue membranes. These changes are considered to accelerate the ageing of the skin. It is also known that immediately after irradiation, UV-A acts to cause melanism of the skin (instant melanism) and can promote the degenerating action of UV-B on the skin. Thus, it is considered that UV-A is one of the factors which cause spots or freckles to be formed or exacerbated.

As will be apparent from the above, it is considered to be important that the skin is protected not only from UV-B, but also from UV-A in order to prevent the promotion of ageing of the skin and the formation or exacerbation of spots or freckles.

However, studies on the action of UV-A on skin have just started and few substances capable of effectively absorbing UV-A are known. Currently known substances are dibenzoylmethane derivatives and cinnamic acid derivatives, most of which are liposoluble (West Germany Patent Application Laid-open Nos. 2728241 and 2728243, and Japanese Patent Application Laid-open Nos. 51-61641, 52-46056 and 57-197209), with only a few water-soluble substances being known (Japanese Patent Application Laid-open No. 57-59840).

The present inventors already proposed in Japanese Patent Application Laid-open No. 60-190708 dibenzoylmethane derivatives which satisfy the following requirements (1) to (8) for a lone wave UV ray absorber.

(1) Have a maximum absorption wavelength at approximately 350 nm.

(2) The molar absorptivity ($\epsilon$) at the above maximum absorption wavelength is sufficiently high.

(3) Since coloration is not favorable upon use as a cosmetic composition, an absorption in a visible light range has to be small, e.g. $\epsilon \approx 0$ over 400 nm.

(4) High heat and light stabilities.

(5) No toxicity, irritativeness and other harmful actions on skin.

(6) Good compatibility with cosmetic base materials.

(7) Being sparingly absorbed percutaneously and removed by perspiration, i.e., having a prolonged efficacy.

(8) Inexpensiveness.

The derivatives are of the following formula (II)

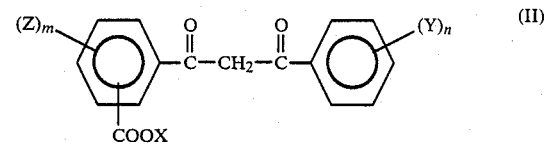

in which X represents a hydrogen atom, a monovalent metal cation, an organic cation, a linear or branched aliphatic hydrocarbon group having from 1 to 24 carbon atoms or a polyoxyethylene or polyoxypropylene oxide group, Ys and Zs may be the same or different and represent a hydroxyl group, a linear or branched aliphatic hydrocarbon group having from 1 to 24 carbon atoms, an alkoxy group having from 1 to 24 carbon atoms or a polyoxyethylene or polyoxypropylene oxide group, and m and n are independently an integer of from 0 to 3.

However, known UV ray absorbers are disadvantageous in that they are dissolved in water, organic solvents, oil substances, sebum and the like, and are percutaneously absorbed or diffused over the skin, so that problems are involved in the safety on the human body and the lasting efficacy. In order to solve the problems, there have been proposed polyvalent metal salts of paramethoxycinnamic acid (Japanese Patent Application Laid-open No. 60-94936) and polyvalent metal salts of paradimethylaminobenzoic acid (Japanese Patent Application Laid-open No. 60-94949). However, these compounds do not absorb UV-A and are not satisfactory in protecting the skin from UV rays.

Accordingly, there is a demand for a long wave UV ray absorber (hereinafter referred to as UV-A absorber) which has an intense UV-A absorption action and overcomes the above problems.

SUMMARY OF THE INVENTION

The present inventors made intensive studies and, as a result, found that a UV-A absorber containing a specific type of dibenzoylmethane derivative is insoluble in water, organic solvents, oily substances and sebum, can be formulated in cosmetics and the like and efficiently absorbs UV-A. The present invention was accomplished based on the above finding.

More particularly, the present invention provides a long wave UV ray absorber which comprises a dibenzoylmethane derivative of the following general formula (I)

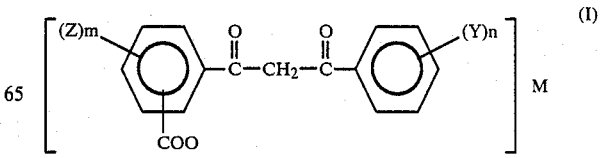

in which Ys and Zs may be the same or different and represent a hydroxyl group, a linear or branched aliphatic hydrocarbon group having from 1 to 24 carbon atoms, an alkoxy group having from 1 to 24 carbon atoms or a polyoxyethylene or polyoxypropylene oxide group, m and n are independently an integer of from 0 to 3, and M represents a polyhydroxylated aluminium ion of the formula $Al_{2+\lambda}(OH)_{3\lambda+5}$ (in which $\lambda$ is a value of from $-1$ to 3). Also, the present invention provides cosmetic compositions formulated with the above absorber.

DETAILED DESCRIPTION OF THE INVENTION AND PREFERRED EMBODIMENTS

In the dibenzoylmethane derivative (I) which is a UV-A absorber component, the polyhydroxylated aluminium ion represented by M includes, for example, $Al(OH)_2{}^+$, $Al_2(OH)_5{}^+$, $Al_3(OH)_8{}^+$, $Al_4(OH)_{11}{}^+$ and $Al_5(OH)_{14}{}^+$. Of these, $Al(OH)_2{}^+$ and $Al_2(OH)_5{}^+$ are preferred.

The dibenzoylmethane derivative (I) used in the invention is prepared, for example, as follows.

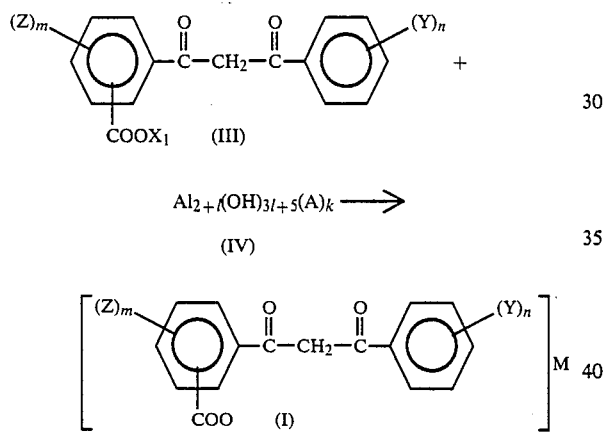

in which $X_1$ is a monovalent cation such as sodium, potassium or ammonium, A represents an anion such as Cl, Br, $NO_3$, $SO_4$ or the like, k is a value of 1 when A is a monovalent anion and a value of ½ when A is a divalent anion, and $\lambda$, m, n, M, Y and Z have, respectively, the same meaning as defined before.

When a dibenzoylmethanecarboxylate (III) and a polyhydroxylated aluminium salt (IV) are reacted in an aqueous solution, the dibenzoylmethane derivative (I) is obtained in the form of a carboxylate of polyhydroxylated aluminium ion.

The starting dibenzoylmethanecarboxylate (III) may be classified into the following eight groups of compounds.

(1) Dibenzoylmethanecarboxylates of the following general formula (V)

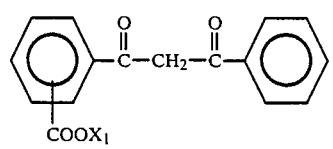

in which $-COOX_1$ may be positioned at the ortho, meta or para position and $X_1$ has the same meaning as defined before.

(2) 4'-Alkoxydibenzoylmethanecarboxylates of the following general formula (VI)

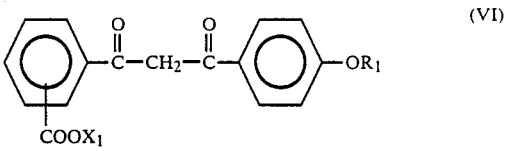

in which $R_1$ represents a hydrogen atom or a hydrocarbon group having from 1 to 18 carbon atoms, preferably a linear or branched alkyl group or alkylene group having from 1 to 4 carbon atoms, which includes methyl, ethyl, vinyl, (iso)propyl, (iso)propenyl, (iso)butyl or (iso)butenyl groups, the substituted position of $-COOX_1$ is the same as defined above, and $X_1$ has the same meaning as defined above.

(3) 3'-Hydroxy-4'-alkoxydibenzoylmethanecarboxylates of the following general formual (VII)

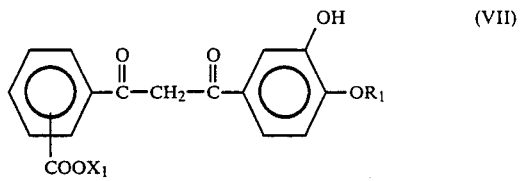

in which the substituted position of $-COOX_1$, $X_1$ and $R_1$ are, respectively, the same as defined before.

(4) 2,3'-Dihydroxy-4'-alkoxydibenzoylmethanecarboxylates of the following general formula (VIII)

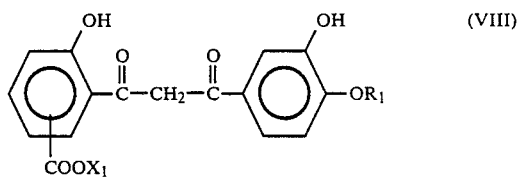

in which the substituted position of $-COOX_1$, $X_1$ and $R_1$ are, respectively, the same as defined before.

(5) 4'-Alkoxy-2-polyoxyethyleneoxydibenzoylmethanecarboxylates of the following general formula (IX)

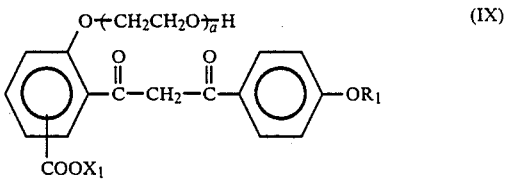

in which the substituted position of $-COOX_1$, $X_1$ and $R_1$ are, respectively, the same as defined before, and a is an integer of from 1 to 10, preferably from 1 to 6.

(6) 3',4'-Bis(polyoxyethyleneoxy)dibenzoylmethanecarboxylates of the following general formula (X)

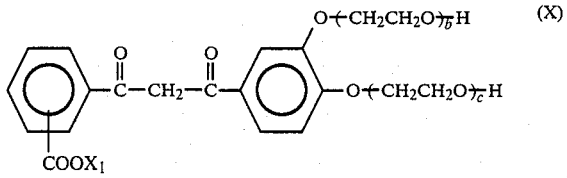

in which the substituted position of $-COOX_1$ and $X_1$ are, respectively, the same as defined before, and b and c are independently an integer of from 1 to 6, preferably from 1 to 3.

(7) 4'-Polyoxyethyleneoxydibenzoylmethanecarboxylates of the following general formula (XI)

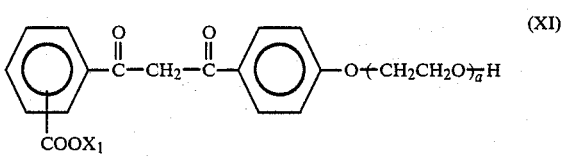

in which the substituted position of $-COOX_1$, $X_1$ and a are, respectively, the same as defined above.

(8) 4'-Alkoxy-3'-polyoxyethyleneoxydibenzoylmethane-carboxylates of the following general formula (XII)

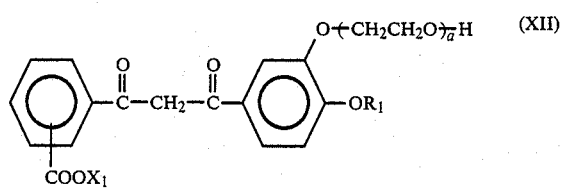

in which the substituted position of $-COOX_1$, $X_1$, $R_1$ and a are, respectively, the same as defined above.

Preferable dibenzoylmethanecarboxylates include, for example, triethanolamine dibenzoylmethane-2-carboxylate, sodium dibenzoylmethane-3-carboxylate, sodium 4'-methoxydibenzoylmethane-2-carboxylate, sodium 4'methoxydiebenzoylmethane-3-carboxylate, ammonium 3'-hydroxy-4'-methoxydibenzoylmethane-2-carboxylate, sodium 2,3'-dihydroxy-4'-methoxydibenzoylmethane-5-carboxylatee, potassium 4'-methoxy-2-polyoxyethyleneoxydibenzoylmethane-5-carboxylate, sodium 3',4'-bis(polyoxyethyleneoxy)-dibenzoylmethane-3-carboxylate, potassium 4'-methoxydibenzoylmethane-4-carboxylate, sodium 4'-polyoxyethyleneoxydibenzoylmethane-4-carboxylate, potassium 4'-methoxy-3'-polyoxyethyleneoxydibenzoylmethane-4-carboxylate, and the like.

The reaction between these dibenzoylmethanecarboxylates (III) and the polyhydroxylated aluminium salts (IV) readily proceeds by addition of an aqueous solution of the polyhydroxylated aluminium salt (IV) to an aqueous solution of the dibenzoylmethanecarboxylate (III). An intended dibenzoylmethane derivative (I) is insoluble in water and is suspended, so that it can be readily separated by filtration and washing. The reaction temperature ranges from room temperature to 90° C. It is preferred that the polyhydroxylated aluminium salt (IV) is added in such an amount that the cationic valences of the polyhydroxylated aluminium are in range of 1.0 to 1.5 equivalents to the dibenzoylmethanecarboxylate (III).

The starting dibenzoylmethanecarboxylate (III) is prepared according to any known processes described, for example, in Ann. Chim. (Rone), 48, 762 (1958), J. Chem. Soc., 2063 (1952), Pestic Sci., 4, 473 (1973), and U.S. Pat. No. 4381360.

The simplest process comprises the steps of subjecting a substituted acetophenone (XIV) to a condensation reaction with monoester (XIII) of substituted phthalic acid (any isomer of an ortho, meta or para compound) in the presence of a base catalyst to obtain a compound (IIIa), and converting the compound (IIIa) into a salt by a usual manner. The reaction proceeds as follows:

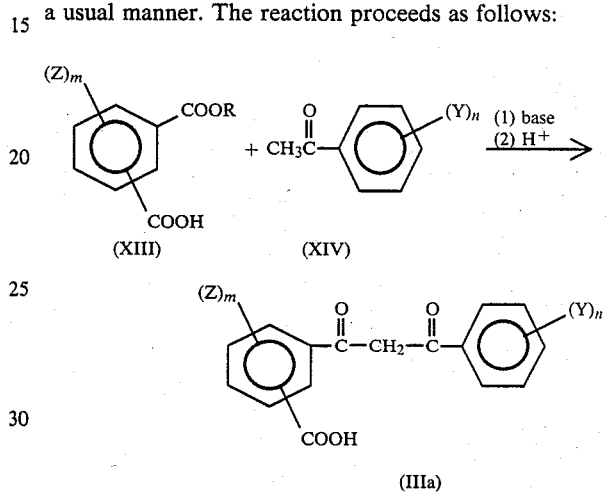

in which R represents a methyl group or an ethyl group, and Y, Z, m and n have, respectively, the same meanings as defined before.

An acid anhydride of the following general formula (XV) may be used instead of the ortho isomer of the monoester (XIII):

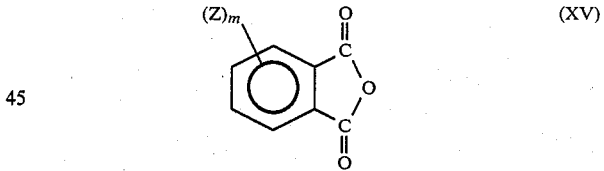

in which Z and m have, respectively, the same meanings as defined before.

The thus obtained dibenzoylmethane derivative (I), which is a UV-A absorber component of the invention, has wide utility in the field where protection from UV rays is necessary. In order to avoid the adverse influence of UV rays on the skin, the derivative may be suitably added to cosmetic compositions, medicines and the like.

The amount of the UV ray absorber in cosmetic compositions may vary depending on the type of cosmetic composition and is generally from 0.1 to 20 wt %, preferably from 0.5 to 10 wt % (hereinafter referred to simply as %), of a cosmetic composition.

For the preparation of cosmetic compositions, a dibenzoylmethane derivative (I) which has high affinity for a known cosmetic base used in each case is suitably selected and formulated by a usual manner. The formulation is prepared in a desired form of a cream, a solution, an oil, a spray, a stick, a milky emulsion, a foundation, an ointment or the like.

The proper selection of a dibenzoylmethane derivative (I) in conformity with the type of the cosmetic base enables one to make all the types of cosmetic compositions having the UV-A absorptivity including base cosmetics; such as cosmetic oils using oil bases, oily creams or oily milky emulsions using a large amount of oils, weak oily creams or milky emulsions using a large amount of water and water-based lotions; foundations using oil bases; and makeup cosmetics such as lipstick. Suitable bases and solvents include, for example, hydrocarbons such as liquid paraffin, crystal oil, ceresin, ozokerite, montan wax and the like; plant and animal oils and fats or waxes such as olive, carnauba wax, lanolin, spermaceti and the like; aliphatic acids or esters such as stearic acid, palmitic acid, oleic acid, glycerine monostearate, glycerine distearate, glycerine monooleate, isopropyl myristate, isopropyl stearate, butyl stearate and the like; and alcohols such as ethyl alcohol, isopropyl alcohol, cetyl alcohol, stearyl alcohol, palmityl alcohol, hexyldodecyl alcohol, and the like. In addition polyhydric alcohols such as glycol, glycerine or sorbitol having the humectant effect may be used.

The cosmetic compositions of the invention may be effective when simply formulated with a dibenzoylmethane derivative (I) as an active ingredient, but other known UV-B absorber may be further added, if necessary. Examples of such UV-B absorbers include p-methylbenzylidene-D,L-camphor or its sodium sulfate salt, sodium 2-phenylbenzimidazole-5-sulfonate, sodium 3,4-dimethylphenylglyoxylate, 4-phenylbenzophenone, isooctyl 4-phenylbenzophenone-2′-carboxylate, p-methoxy cinnamate, 2-phenyl-5-methylbenzoxazole, p-dimethyl aminobenzoate and the like.

The cosmetic compositions of the invention may further comprise, aside from the above-described ingredients, various additives. Suitable additives include, for example, W/O type and O/W type emulsifiers. The emulsifiers may be any commercially available emulsifiers. Thickeners such as methyl cellulose, ethyl cellulose, carboxymethyl cellulose, polyacrylic acid, tragacanth gum, agar-agar, gelatin and the like may be used as the additive. If necessary, perfumes, preservatives, humectants, emulsion stabilizers, medical ingredients and/or physiologically allowable colorants may be added.

The UV-A absorber of the invention can effectively shut out UV-A which causes a harmful action on skin and can thus protect the skin, and is stable against light and heat over a long time. The absorber is insoluble in water, organic solvents, oily substances, sebum and the like, so that percutaneous absorption does hardly take place and the absorber is scarcely removed by water or sweat, thus keeping a high efficacy. Accordingly, the cosmetic compositions comprising the compound have similar good effects.

In general, when dissolved in a solvent, 1,3-diketones such as dibenzoylmethane may undergo considerable changes in maximum absorption wavelength and molar absorptivity coefficient depending on the polarity of the solvent. The compounds of the present invention which are insoluble in solvents are not susceptible of the influence of the polarity of a solvent and can thus effectively protect the skin from UV-A rays.

The present invention is described in detail by way of examples and test examples.

EXAMPLE 1

Preparation of

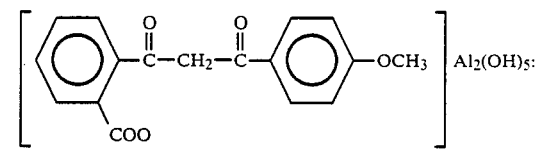

100 ml of water was added to 8.90 g of 4′-methoxydibenzoylmethane-2-carboxylic acid, to which 30 ml of 1N NaOH was added for dissolution. The solution was heated to 70° C., to which a solution of 7.0 g of Al$_2$(OH)$_5$Cl•3H$_2$O in 300 ml of water heated to 70° C. was added, followed by agitation for 30 minutes and cooling down to room temperature. After filtration, the resultant product was washed with water and methanol, thereby obtaining 11.4 g of the captioned compound in the form of a light yellow powder.

EXAMPLE 2

Preparation of

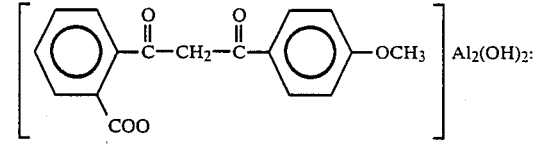

100 ml of water was added to 8.90 g of 4′-methoxydibenzoylmethane-2-carboxylic acid, to which 30 ml of 1N NaOH was added for dissolution. The solution was heated to 70° C. 7.20 g of Alcl$_3$•6H$_2$O was added to 100 ml of water, to which was further added 25.0 ml of 1N NaOH. The mixture was uniformly dissolved and heated to 70° C. This solution was added to the first solution and agitated for 30 minutes, and was cooled down to room temperature, followed by filtration and washing with water and methanol, thereby obtaining 12.5 g of the captioned compound as a light yellow powder.

EXAMPLE 3

Preparation of

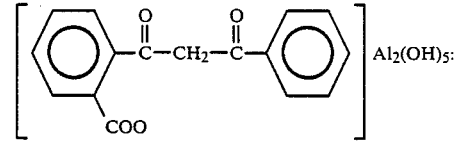

The procedure of Example 1 was repeated except that 8.0 g of dibenzoylmethane-2-carboxylic acid was used instead of 4′-methoxy-dibenzoylmethane-2-carboxylic acid, thereby obtaining 9.0 g of the captioned compound as a white powder.

EXAMPLE 4

Preparation of

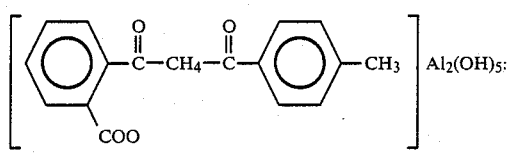

The procedure of Example 1 was repeated except that 8.42 g of 4'-methyldibenzoyl-methane-2-carboxylic acid was used instead of 4'-methoxydibenzoylmethane-2-carboxylic acid, thereby obtaining 8.9 g of the captioned compound as a white powder.

EXAMPLE 5

Preparation of

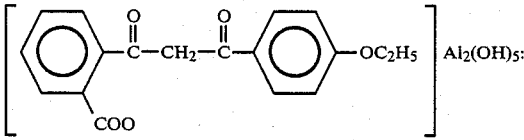

The procedure of Example 1 was repeated except that 9.32 g of 4'-ethoxydibenzoyl-methane-2-carboxylic acid was used instead of 4'-methoxydibenzoylmethane-2-carboxylic acid, thereby obtaining 8.7 g of the captioned compound as a light yellow powder.

EXAMPLE 6

Preparation of

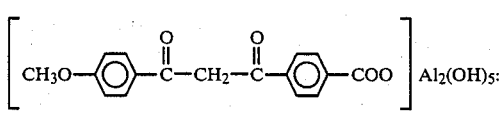

The procedure of Example 1 was repeated except that 8.90 g of 4'-methoxydibenzoyl-methane-4-carboxylic acid was used instead of 4'-methoxydibenzoylmethane-2-carboxylic acid, thereby obtaining 4.1 g of the captioned compound as a yellow powder.

TEST EXAMPLE 1

UV-A absorbers indicated in Table 1 were each weighed in 5 mg and subjected to ultrasonic treatment for 5 minutes in 50 ml of hexane, followed by measurement of an absorbance by means of an automatic spectrophotometer, Model MPS-2000 made by Shimadzu K. K., using a 10 mm quartz cell. The results are shown in Table 1 below.

TABLE 1

| Compound | Wavelength and Absorbance | | | | | | |
|---|---|---|---|---|---|---|---|
| | 280 | 300 | 320 | 340 | 360 | 380 | 400 |
| Inventive Products | | | | | | | |
| UV-A absorber of Example 1 | 0.947 | 0.890 | 0.815 | 1.076 | 1.144 | 1.024 | 0.634 |
| UV-A absorber of Example 2 | 0.466 | 0.410 | 0.401 | 0.568 | 0.640 | 0.635 | 0.486 |
| UV-A absorber of Example 3 | 0.673 | 0.655 | 0.833 | 1.065 | 1.149 | 0.949 | 0.451 |
| UV-A absorber of Example 4 | 0.553 | 0.462 | 0.611 | 0.848 | 0.884 | 0.703 | 0.319 |
| UV-A absorber of Example 5 | 1.048 | 0.950 | 0.867 | 1.189 | 1.267 | 1.120 | 0.642 |
| UV-A absorber of Example 6 | 0.494 | 0.466 | 0.522 | 0.660 | 0.699 | 0.629 | 0.472 |
| Comparative Products | | | | | | | |
| $[CH_3O-C_6H_4-CH=CH-COO]_2Ca$ | 0.060 | 0.060 | 0.051 | 0.027 | 0.017 | 0.013 | 0.010 |
| $[CH_3O-C_6H_4-CH=CH-COO]_2Mg$ | 0.041 | 0.041 | 0.036 | 0.017 | 0.013 | 0.009 | 0.007 |

EXAMPLE 7

Suspension Type Lotion:
(Formulation)

| | |
|---|---|
| (1) Ethanol | 10(%) |
| (2) Glycerine | 4 |
| (3) [Dibenzoylmethane-2-carboxylic acid] Al(OH)₂ | 5.5 |
| (4) Camphor | 0.15 |
| (5) Perfume | very small amount |
| (6) Purified water | balance |

(Preparation)

Ingredients (1), (2),(3) and (5) were mixed and suspended, which was added to (6) in which ingredient (4) was dissolved in advance, followed by sufficient agitation to obtain a suspension type lotion.

EXAMPLE 8

W/O-type Cream:
(Formulation)

| | |
|---|---|
| (1) Dibenzoylmethane derivative of Example 1 | 8(%) |
| (2) Vaseline | 6 |
| (3) Cholesterol | 0.6 |
| (4) Cetanol | 0.5 |
| (5) Sorbitan sesquioleate | 2 |
| (6) Liquid lanolin | 4 |
| (7) Isopropyl palmitate | 8 |
| (8) Squalane | 10 |
| (9) Solid paraffin | 4 |
| (10) Glycerine | 3 |
| (11) Preservative | suitable amount |
| (12) Perfume | very small amount |
| (13) Purified water | balance |

(Preparation)

Ingredients (1) to (9) were mixed under agitation at 80° C. to obtain an oil phase portion. The other ingredients were mixed and heated for dissolution at 80° C. and added to the oil phase portion for preemulsification. The mixture was uniformly emulsified by means of a homomixer and cooled down to 30° C. to obtain a product.

EXAMPLE 9

O/W-type Cream:
(Formulation)

| | | |
|---|---|---|
| (1) | Beeswax | 5.5(%) |
| (2) | Cetanol | 4.5 |
| (3) | Hydrogenated lanolin | 7 |
| (4) | Squalane | 33 |
| (5) | Fatty acid glycerine | 3.5 |
| (6) | Oleophilic glycerine monostearate | 2 |
| (7) | Polyoxyethylene sorbitan monolaurate (20 E.O.) | 2 |
| (8) | Dibenzoylmethane derivative of Example 2 | 8 |
| (9) | Perfume | very small amount |
| (10) | Preservative | suitable amount |
| (11) | Antioxidant | suitable amount |
| (12) | Propylene glycol | 4.5 |
| (13) | Purified water | suitable amount |

(Preparation)
Ingredients (8), (10), (12) and (13) were mixed under agitation and maintained at 80° C. The other ingredients were mixed and heated for dissolution at 80° C. The firstly prepared aqueous phase portion was added to the oil phase portion for pre-emulsification, followed by uniform emulsification by means of a homomixer and cooling down to 30° C. to obtain a product.

EXAMPLE 10

Foundation Stick:
(Formulation)

| | | |
|---|---|---|
| (1) | Dibenzoylmethane derivative of Example 3 | 10(%) |
| (2) | Titanium oxide (rendered hydrophobic) | 10 |
| (3) | Kaolin | 11.2 |
| (4) | Talc | 10 |
| (5) | Red iron oxide | 1.0 |
| (6) | Yellow iron oxide | 2.5 |
| (7) | Black iron oxide | 0.3 |
| (8) | Liquid paraffin | 18 |
| (9) | Liquid lanolin | 4.5 |
| (10) | Isopropyl myristate | 15 |
| (11) | Microcrystalline wax | 4.5 |
| (12) | Ceresin | 10 |
| (13) | Carnauba wax | 2 |
| (14) | Sorbitan sesquioleate | 1 |

(Preparation)
Ingredients (1) to (11) were heated at 80° C., agitated and mixed, followed by pouring into a mold, cooling and molding to obtain a product.

EXAMPLE 11

Powder Foundation:
(Formulation)

| | | |
|---|---|---|
| (1) | Mica | balance (%) |
| (2) | Dibenzoylmethane derivative of Example 4 | 10 |
| (3) | Talc | 20 |
| (4) | Titanium oxide | 10 |
| (5) | Red iron oxide | 0.8 |
| (6) | Yellow iron oxide | 2.5 |
| (7) | Black iron oxide | 0.1 |
| (8) | Liquid paraffin | 8 |
| (9) | Beeswax | 2 |
| (10) | Preservative | suitable amount |
| (11) | Perfume | very small amount |

(Preparation)
Ingredients (1) to (7) were mixed and milled. The mixture was placed in a high-speed blender, to which a solution obtained by mixing ingredients (8) to (10) at 80° C. was added and mixed. Followed by milling and passing through a screen. The resultant powder was placed in a metal dish and molded.

EXAMPLE 12

Creamy Foundation:
(Formulation)

| | | |
|---|---|---|
| (1) | Stearic acid | 5(%) |
| (2) | Oleophilic glycerine monostearate | 2.5 |
| (3) | Cetostearyl alcohol | 1 |
| (4) | Propylene glycol monolaurate | 3 |
| (5) | Squalane | 7 |
| (6) | Olive oil | 8 |
| (7) | Purified water | balance |
| (8) | Preservative | suitable amount |
| (9) | Triethanolamine | 1.2 |
| (10) | Sorbitol | 3 |
| (11) | Titanium oxide | 10 |
| (12) | Talc | 5 |
| (13) | Coloring pigment | suitable amount |
| (14) | Dibenzoylmethane derivative of Example 5 | 8 |
| (15) | Perfume | very small amount |

(Preparation)
Ingredients (11) to (14) were mixed and milled. Separately, a solution of aqueous phase ingredients (7) to (10) was prepared, to which the milled pigment was added for dispersion and heated to 75° C. Oil phase ingredients (1) to (6) were heated at 80° C. for dissolution, which was added to the aqueous phase under agitation and emulsified. The resultant emulsion was cooled, under agitation, down to 50° C. at which ingredient (15) was added, followed by cooling under agitation to obtain a product.

What is claimed is:
1. A cosmetic composition comprising 0.1 to 20 weight % of a long wave UV ray absorber containing a dibenzoylmethane derivative of the following general formula (I)

$$\left[ (Z)_m \underset{COO}{\bigcirc} \overset{O}{\underset{\|}{C}} - CH_2 - \overset{O}{\underset{\|}{C}} - \bigcirc (Y)_n \right] M \quad (I)$$

in which Ys and Zs may be the same or different and represent a hydroxyl group, a linear or branched aliphatic hydrocarbon group having from 1 to 24 carbon atoms, an alkoxy group having from 1 to 24 carbon atoms or a polyoxyethylene or polyoxypropylene oxide group, m and n are independently an integer of from 0 to 3, and M represents a polyhydroxylated aluminium ion of the formula $Al_{2+\lambda}(OH)_{3\lambda+5}$, in which $\lambda$ is a value of from $-1$ to 3, in admixture with an inert cosmetic carrier.

2. The long wave UV ray absorber of claim 1, wherein said polyhydroxylated aluminium ion is selected from the group consisting of $Al(OH)_2+$, $Al_2(OH)_5+$, $Al_3(OH)_8+$, $Al_4(OH)_{11}+$ and $Al_5(OH)_{14}+$.

3. The UV ray absorber of claim 3, wherein said polyhydroxylated aluminium ion is selected from the group consisting of $Al(OH)_2+$ and $Al_2(OH)_5+$.

4. The UV ray absorber of claim 1, wherein the dibenzoylmethanecarboxylate portion of said dibenzoylmethane derivative is obtained from a member selected from the group consisting of triethanolamine dibenzoylmethane-2-carboxylate, sodium dibenzoylmethane-3-carboxylate, sodium 4'-methoxydibenzoylmethane-2-carboxylate, sodium 4'-methoxydibenzoylmethane-3-carboxylate, ammonium 3'-hydroxy-4'-methoxydibenzoylmethane-2-carboxylate, sodium 2,3'-dihydroxy-4'-methoxydibenzoylmethane-5-carboxylate, potassium 4'-methoxy-2-polyoxyethyleneoxydibenzoylmethane-5-carboxylate, sodium 3',4'-bis(polyoxyethyleneoxy)-dibenzoylmethane-3carboxylate, potassium 4'-methoxydibenzoylmethane-4-carboxylate, sodium 4'-polyoxyethleneoxydibenzoylmethane-4-carboxylate, and potassium 4'-methoxy-3'-polyoxyethyleneoxydibenzoylmethane-4-carboxylate.

* * * * *